(12) United States Patent
Meng et al.

(10) Patent No.: US 11,806,524 B2
(45) Date of Patent: Nov. 7, 2023

(54) BIMODAL HYBRID COCHLEAR IMPLANTS

(71) Applicant: Massachusetts Eye and Ear Infirmary, Boston, MA (US)

(72) Inventors: Xiankai Meng, Boston, MA (US); Daniel J. Lee, Boston, MA (US); Albert Edge, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 507 days.

(21) Appl. No.: 16/630,001

(22) PCT Filed: Jul. 16, 2018

(86) PCT No.: PCT/US2018/042315
§ 371 (c)(1),
(2) Date: Jan. 10, 2020

(87) PCT Pub. No.: WO2019/014680
PCT Pub. Date: Jan. 17, 2019

(65) Prior Publication Data
US 2021/0085963 A1 Mar. 25, 2021

Related U.S. Application Data

(60) Provisional application No. 62/532,944, filed on Jul. 14, 2017.

(51) Int. Cl.
*A61N 1/05* (2006.01)
*A61N 1/36* (2006.01)
*A61N 5/06* (2006.01)

(52) U.S. Cl.
CPC ....... *A61N 1/0541* (2013.01); *A61N 1/36038* (2017.08); *A61N 5/0622* (2013.01); *A61N 2005/0652* (2013.01); *A61N 2005/0663* (2013.01)

(58) Field of Classification Search
CPC .............. A61N 1/0541; A61N 1/36038; A61N 5/0622; A61N 2005/0652; A61N 2005/0663
See application file for complete search history.

(56) References Cited

U.S. PATENT DOCUMENTS

| | | | | |
|---|---|---|---|---|
| 4,408,608 A | * | 10/1983 | Daly | A61N 1/372 607/57 |
| 6,445,805 B1 | * | 9/2002 | Grugel | H04R 25/65 181/129 |
| 6,829,509 B1 | * | 12/2004 | MacDonald | A61N 1/086 600/374 |
| 7,883,536 B1 | * | 2/2011 | Bendett | A61N 5/0622 607/88 |
| 8,012,189 B1 | * | 9/2011 | Webb | A61N 5/0603 607/88 |

(Continued)

OTHER PUBLICATIONS

Appler et al., "Gata3 is a critical regulator of cochlear wiring," J. Neurosci., Feb. 2013, 33(8):3679-3691.

(Continued)

*Primary Examiner* — Christopher A Flory
(74) *Attorney, Agent, or Firm* — Fish & Richardson P.C.

(57) ABSTRACT

The invention relates to multimodal, e.g., bimodal, hybrid cochlear implants that provide both optical (optogenetic) as well as electrical stimulation to enhance sensitivity.

16 Claims, 13 Drawing Sheets

(56) References Cited

U.S. PATENT DOCUMENTS

| | | | |
|---|---|---|---|
| 8,747,447 B2* | 6/2014 | Stafford | A61N 1/36039 607/88 |
| 8,843,217 B1* | 9/2014 | Keller | A61N 5/0622 607/137 |
| 2008/0140149 A1* | 6/2008 | John | A61B 8/0808 607/45 |
| 2010/0034409 A1* | 2/2010 | Fay | H04R 25/554 381/326 |
| 2010/0048982 A1* | 2/2010 | Puria | H04R 25/602 607/57 |
| 2010/0114190 A1* | 5/2010 | Bendett | A61N 5/0622 607/3 |
| 2010/0174329 A1 | 7/2010 | Dadd et al. | |
| 2010/0174330 A1* | 7/2010 | Dadd | A61N 5/0622 607/3 |
| 2010/0174344 A1* | 7/2010 | Dadd | A61N 5/0601 607/57 |
| 2010/0280307 A1* | 11/2010 | Lineaweaver | A61N 1/36038 607/57 |
| 2010/0292758 A1* | 11/2010 | Lee | A61N 5/0622 607/55 |
| 2011/0125222 A1* | 5/2011 | Perkins | A61N 5/0601 607/61 |
| 2011/0144719 A1* | 6/2011 | Perkins | A61N 1/36038 607/57 |
| 2011/0152976 A1* | 6/2011 | Perkins | H04R 25/606 607/92 |
| 2011/0172725 A1* | 7/2011 | Wells | A61N 1/36017 607/3 |
| 2011/0295331 A1 | 12/2011 | Wells et al. | |
| 2011/0295347 A1* | 12/2011 | Wells | A61N 5/0622 607/89 |
| 2012/0197374 A1 | 8/2012 | Vogt et al. | |
| 2013/0006328 A1* | 1/2013 | Bouchataoui | H04R 25/606 607/57 |
| 2013/0023962 A1* | 1/2013 | Stafford | A61N 1/36039 607/88 |
| 2013/0023967 A1 | 1/2013 | Stafford et al. | |
| 2013/0144354 A1* | 6/2013 | Dadd | A61N 5/0601 607/3 |
| 2013/0287239 A1* | 10/2013 | Fay | H04R 25/554 381/326 |
| 2014/0094864 A1 | 4/2014 | Ambett et al. | |
| 2014/0228901 A1* | 8/2014 | Vogt | A61N 1/36038 607/92 |
| 2014/0296937 A1* | 10/2014 | Goldsmith | A61N 1/36038 607/57 |
| 2018/0125415 A1* | 5/2018 | Reed | A61B 5/125 |
| 2018/0234776 A1* | 8/2018 | Fung | H04S 1/005 |
| 2018/0369606 A1* | 12/2018 | Zhang | A61B 5/4836 |

OTHER PUBLICATIONS

Druckenbrod & Goodrich, "Sequential Retraction Segregates SGN Processes during Target Selection in the Cochlea," J. Neurosci., Dec. 2015, 35(49):16221-16235.

Hernandez et al., "Optogenetic stimulation of the auditory pathway," J. Clin. Invest., Mar. 2014, 124(3)1114-1129.

Liu et al.,"Heterogeneous intrinsic excitability of murine spiral ganglion neurons is determined by Kv1 and HCN channels," Neuroscience, Jan. 2014, 257:96-110.

Madisen et al., "A toolbox of Cre-dependent optogenetic transgenic mice for light-induced activation and silencing," Nat. Neurosci., May 2012, 15(5):793-802.

Meng al., "Abstract: Optogenetic Modulated Electrical Stimulation: a Novel Co-Stimulation Paradigm for a Multichannel Cochlear Implant," Presented at Proceedings of the Association for Research in Otolaryngology Midwinter Conference, San Diego, CA, Feb. 10-14, 2018, 1 page.

Meng et al., "Abstract: Mechanisms associated with optogenetic control of spiral ganglion neurons," Presented at the Conference on Implantable Auditory Prostheses (CIAP), Lake Tahoe, CA, Jul. 16-21, 2017, 1 page.

PCT International Preliminary Report on Patentability in International Appln. No. PCT/US2018/0423315, dated Jan. 14, 2020, 6 pages.

PCT International Search Report and Written Opinion in International Appln. No. PCT/US2018/042315, dated Oct. 22, 2018, 12 pages.

* cited by examiner

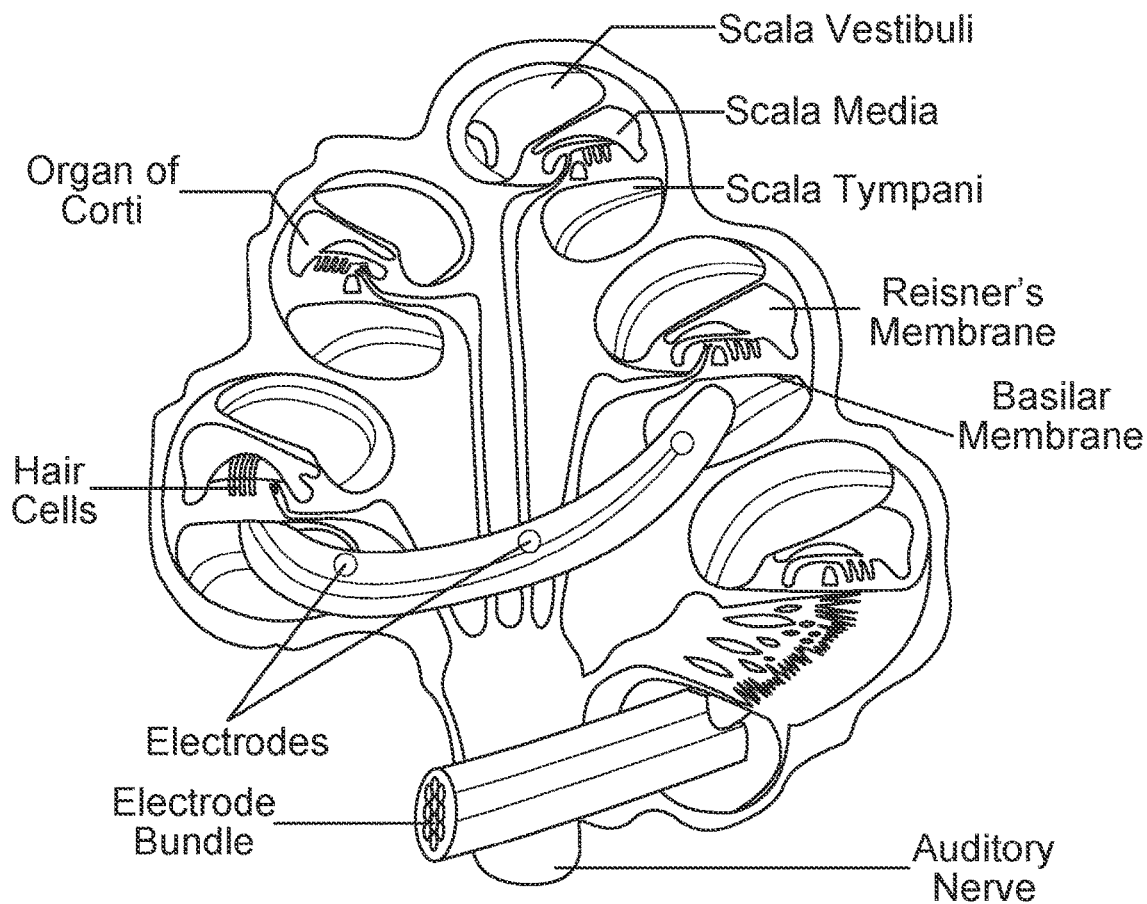
FIG 1 (Prior Art)
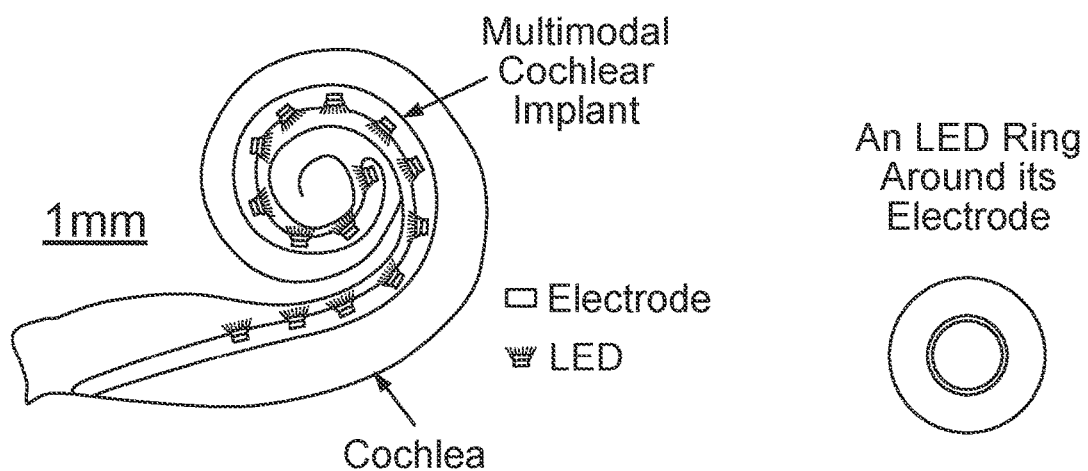
FIG. 2A
FIG. 2B

The Optogenetic Threshold is Defined as the Light Level to Generate an Action Potential, $\theta_0$=164.56uW The Electrical Threshold is Defined as the Current Level to Generate an Action Potential, $\theta_e = 8pA$ Electrodes Placement Stimulation Paradigm P1 Amplitude Shift

BIMODAL HYBRID COCHLEAR IMPLANTS

CROSS-REFERENCE TO RELATED APPLICATIONS

This application is a 371 U.S. National Phase Application of PCT/US2018/042315, filed on Jul. 16, 2018, which claims the benefit of priority under 35 U.S.C. Section 119(e) to U.S. Provisional Patent Application No. 62/532,944, filed on Jul. 14, 2017, the entire contents of which are incorporated herein by reference.

STATEMENT AS TO FEDERALLY SPONSORED RESEARCH

This invention was made with Government support under Grant R21 DC-012422-02 and R01 DC-007174) awarded by the National Institutes of Health, and additional support by the Bertarelli Foundation. The Government has certain rights in the invention.

TECHNICAL FIELD

This invention relates to cochlear implants.

BACKGROUND

A cochlear implant is an electronic device that is implanted into the inner ear to restore auditory perception, at least partially, to the deaf and hard-of-hearing. Cochlear implants create auditory sensation by generating electric field gradients in the area of the peripheral nerve fibers of the auditory nerve bundle. This bundle contains approximately 30,000 individual afferent nerve fibers normally linked to approximately 4,500 inner hair cells. Sound signals are picked up by a microphone within the implant, converted into digital signals, and processed by a signal processor in order to activate different stimulation channels. These channels, in turn, stimulate different groups of nerve fibers within the auditory nerve.

The ear is composed of four main sections: the external ear, middle ear, inner ear, and the transmission pathway to the hearing center in the brain. In normal hearing, sound waves travel along the external ear canal and cause the tympanic membrane (also called the ear drum) to vibrate. The three small bones of the middle ear (the malleus, incus, and stapes) transmit these vibrations to the cochlea of the inner ear. The cochlea is divided along its length by a basilar membrane that distributes vibrational energy longitudinally by frequency. The lowest frequencies cause maximum membrane motion near the cochlea's apex, and the highest frequencies maximize motion near the base. Four parallel rows of hair cells extend along the length of the basilar membrane and, when vibrated, transduce acoustic signals into electrical impulses carried to the brain by auditory nerve fibers (see FIG. 1).

Optogenetic stimulation, which is the use of light to control cells, such as neurons, in living tissue, has shown promise in the improvement of frequency resolution in a multichannel auditory prosthesis such as a cochlear implant. However, the mechanisms accounting for optogenetic activation of spiral ganglion neurons (SGNs) remain unclear.

SUMMARY

This disclosure is based, at least in part, on the discovery that if one makes a multimodal, e.g., bimodal, hybrid cochlear implant that provides both optical (e.g., optogenetic) and electrical stimulation to spiral ganglion neurons, then the implant can provide better sensitivity compared to implants that provide only electrical stimulation.

In general, the disclosure features devices for treating hearing loss, methods of making the devices, and methods for treating hearing loss. The devices include cochlear implants that provide both optical and electrical stimulation. While cochlear implants are described further below, we note here that they include electrodes that bypass dead or damaged hair cells in the cochlea by directly stimulating the auditory nerve fibers leading to the perceptions of sound.

The new bimodal hybrid cochlear implants can overcome some limitations of pure optogenetic stimulation. For example, they reduce the effect from long time overexcitement. The can also utilize a sub-threshold level of blue light, which can save some power and require lower expression levels of opsins.

In one aspect, the disclosure features bimodal hybrid cochlear implants including an elongated, flexible housing sized to fit within a human or animal cochlea; a wire extending longitudinally through the housing to carry an electrical signal; an electrode bundle arranged with the housing, e.g., within a lumen extending longitudinally within the housing, wherein each electrode in the electrode bundle is in electrical contact with the wire and wherein the electrodes are arranged such that an end of each electrode exits the housing or can emit an electrical signal through the housing; a plurality of light emitters, wherein each light emitter is arranged to emit light from the housing when implanted into the cochlea; and a controller linked to the wire and the light emitters and arranged to control emission of electrical signals from the electrodes and emission of light signals from the light emitters, wherein the light signal is controlled to be emitted prior to the electrical signal.

In certain implementations, the array of electrodes is a linear array of electrodes and in certain embodiments, the ends of the electrodes are arranged on an external surface of the flexible housing.

In some implementations, the light signal is controlled to be emitted prior to and overlapping with the electrical signal. In various embodiments, the implant includes at least 2 to about 30 electrodes, e.g., 5, 10, 15, 18, 20, 22, 24, 26, or 28 electrodes, and at least 2 to about 30, e.g., 5, 10, 15, 18, 20, 22, 24, 26, or 28 light emitters. In some embodiments, the light emitters emit blue light, e.g., at a wavelength of about 473 nm.

In certain implementations, the light emitters are light emitting diodes (LEDs), and each LED is in electrical contact with the wire and is arranged to emit light from the housing when implanted into the cochlea. The LEDs can emit blue light, e.g., at a wavelength of about 473 nm.

In other implementations, the light emitters comprise a light source and a plurality of optical fibers arranged within the housing such that ends of each optical fiber emit light through a wall of the housing or through windows or openings arranged in the wall of the housing, and wherein the controller is linked to the light source.

In another aspect, the disclosure features methods of treating a subject who has experienced hearing loss. These methods include implanting the bimodal hybrid cochlear implants as described herein. For example, the subject may have hearing loss that is not significantly improved by the use of an external hearing aid. In some embodiments, the hearing loss is severe or profound.

In certain embodiments, the methods further include, prior to implanting the modified cochlear implant, identifying a human subject in need of treatment. Human subjects who are candidates for treatment with a cochlear implant can have unilateral or bilateral hearing loss, and/or severe or profound hearing loss. The human can be a child, e.g., having an age of from between about 12 months and 18 years, or the human can be an adult over the age of 18 years. Following treatment with a cochlear implant disclosed herein, the human can follow a rehabilitation regimen, where the implantee builds skills, including hearing, speech, and language skills. The rehabilitation regimen can be maintained for 6 months, one year, or longer than a year. The human subject can attend rehabilitation sessions more frequently in the months immediately following implantation of the device and less frequently as skill levels become more advanced.

In another aspect, the disclosure provides the hybrid implants as described herein for use in treating a subject who has experienced hearing loss.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a schematic diagram illustrating a generic cochlear implant (shown in black) positioned within a patient, bypassing the normal pathways of the ear canal and the three bones of the middle ear (Eddington and Pierschalla, "Cochlear Implants: Restoring Hearing to the Deaf," On the Brain (The Harvard Mahoney Neuroscience Institute Letter) Vol. 3, No. 4, Fall 1994).

FIG. 2A is a schematic diagram of a bimodal hybrid cochlear implant as described herein.

FIG. 2B is a schematic cross-sectional diagram of an opto-electrical channel combined with an LED ring around its corresponding electrode.

FIG. 3A shows a cross-section through the modiolus from a Bhlhb5-ChR2R heterozygous mouse cochlea showing ChR2R-eYFP (anti-GFP in green) expressed in almost all type I signal ganglion neurons (SGNs) (labeled by class III β tubulin antibody Tuj in red). The yellow shows double labeling. Inset, with similar immunostaining, shows a high-power view of type I SGN cell bodies from a whole-mount of a Bhlhb5-ChR2R homozygous cochlea. FIG. 3B shows a whole-mount of a portion of the organ of Corti. ChR2R-eYFP (in green) is strongly expressed in radially oriented type I afferent fibers and spirally oriented type II afferent fibers. Expression was also observed in olivocochlear fibers ("Efferents") near inner hair cells (IHCs), which were labeled by anti-choline acetyltransferase (ChAT, in red). Inner and outer hair cells did not show expression (labeled blue by Myo7a antibody).

FIG. 4A is a graph showing auditory brainstem responses (ABRs) thresholds vs. frequency for a pure tone test in homozygous (n=5), heterozygous (n=6), and control (n=5) mice. FIGS. 4B and D are graphs of acoustically-evoked (click sound) ABRs (aABRs) and optically-evoked ABRs (oABRs), respectively. FIG. 4C is a photograph of a cochleostomy made in the lateral wall of the left cochlea for optic fiber placement to deliver light to the inner ear.

FIG. 5A is a graph of photocurrent. FIG. 5B is a graph of photodepolarization. FIG. 5C is a microscope photo of whole cell recording. FIG. 5D is a graph of sub-threshold depolarization.

FIG. 6A is a graph of electrical current threshold and FIG. 6B is a graph of sub-threshold optogenetic facilitation.

FIG. 7A is a graph that shows sub-threshold blue light pulses (21.24 µW) together with current injection. FIG. 7B is a graph that indicates electrical threshold shifts and shows the results of several co-stimulation conditions that were tested: No light; "Simu" means light and current were applied at the same time; or light was presented ahead of current injection 2 or 5 ms earlier at two levels: 413 µW (2.5V) and 429 µW (5V).

FIG. 8A is a series of graphs that show co-stimulation. FIG. 8B is an image showing electrode placement. FIG. 8C is a schematic graph showing the stimulation paradigm of electrical shocks and blue laser pulses. FIG. 8D is a graph showing P1 amplitude shift vs. current level.

FIGS. 9A and 9B show ABR waveforms with peaks computed and marked (red and blue squares for positive and negative peak 1 resp.). In FIG. 9A, a supra-threshold level of light (2.5 mW) with a current level of 0.06 mA, and in FIG. 9B, a near-threshold level of light (1 mW) with a current level of 0.06 mA, were used to activate auditory nerves. Artifacts resulting from electrical stimulation were blanked out from ABRs. FIGS. 9C and 9D are bar plots of the peak-to-peak amplitudes extracted from ABRs in 9A and 9B, respectively, and their summation analysis. Bars from left to right show peak amplitudes from ABR evoked with: optical stimulation alone, electrical stimulation alone, co-stimulation and the computed sum from either modality alone. Data were collected from three Bhlhb5-ChR2R-eYFP mice.

FIG. 10A is a graph showing an example of ABRs evoked by a co-stimulation paradigm when the electric pulse is presented just prior to the light pulse. Colors are indicated in FIG. 10B, which is a bar plot of ABR peak amplitude analysis. FIG. 10C is a plot of peak amplitude obtained from co-stimulation against the sum of the peak amplitudes from either modality alone. Black corresponds to the paradigm presenting the electric pulse after the light pulse and red corresponds to the paradigm presenting the electric pulse just prior to the light pulse. Results were computed across all stimulation level combinations (electrical levels represented by different markers). Data were collected from three Bhlhb5-ChR2R-eYFP mice.

DETAILED DESCRIPTION

Figure 3A:
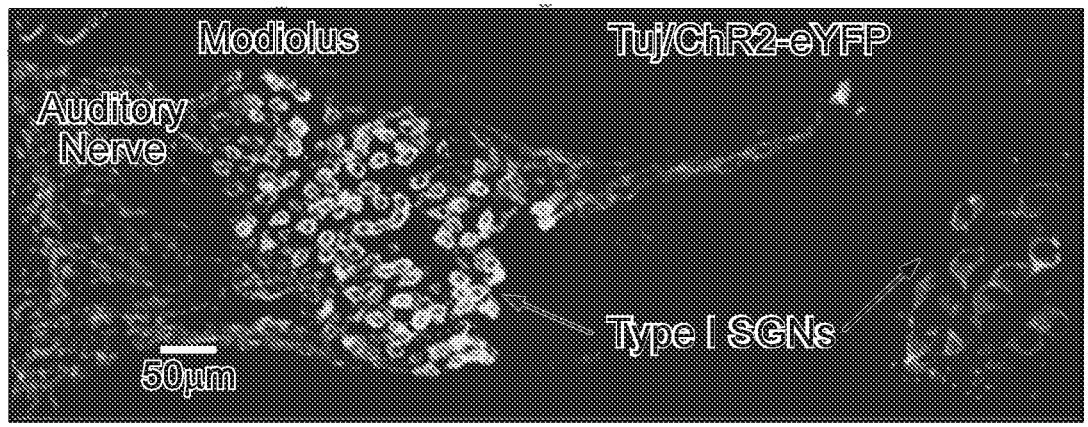
FIGS. 3A-3B are photo micrographs generated from a transgenic mouse model.

We now further describe devices and methods for treating deafness and hearing loss in a human. The devices are bimodal cochlear implants and bimodal cochlear implant electrodes that have been designed to generate both optical and electrical stimulation, and the methods include implantation of such devices.

The outcome of known multichannel cochlear implants is limited by their poor ability to provide frequency and intensity discrimination. Subsequently, known cochlear implant users find it hard to understand speech in noisy environments and to appreciate music. The reason for this problem is that electrical stimulation cannot provide precise activation as the normal hair cell synapses do. In addition, the known implants cannot fully utilize the nature of the human auditory nerve. Every single auditory fiber, i.e., spiral ganglion neuron (SGN), has its own specific activation threshold, and this property is largely varied among different SGNs. This nature gives the auditory nerve the ability to code a huge scale of sound intensity (0 to ~120 dB). However, in the current multichannel implants, the electrical current intensity cannot go to very high levels to activate the fibers with high thresholds, due to the electricity spread between adjacent channels. This fact has constrained people from adding more channels to give users a better frequency experience.

To solve these problems, the current disclosure provides adding optogenetic stimulation in a cochlear implant or implant electrode to improve the sensitivity of neurons to electrical signals, and to enhance the ability to discriminate subtle changes in frequency or intensity.

Optogenetic stimulation relies on photosensitive ion channels (ChR2, Chronos) and can easily excite the neurons. The photosensitive ion channels, in other words, the opsins, can be opened by specific blue light. For example, ChR2 can be opened by blue light at about 473 nm, and allows cations (Na+, K+, Ca2+ . . . ) to fluctuate into the cellular plasma, and depolarize the neuronal membrane. When the membrane potential rises over the threshold of voltage-gated ion channels, especially the voltage-gated sodium channel (Na+ v), the action potential generation process will begin. The whole cell recording studies described herein provide strong evidence to support the optogenetic activation of SGNs.

The experiments described below, including the whole cell recording experiments, demonstrate that electrical stimulation excites the auditory nerve by changing the membrane potential of SGNs as well. The fast change in the electromagnetic field opens the voltage-gated ion channels, e.g., Na+v, K+v and HCN, initiates the depolarization process, pushes the membrane potential to go over the threshold, and evokes action potentials in SGNs.

Based on these findings, optogenetic stimulation also relies on the regular action potential generation machinery, which means, optical stimulation opens the opsins on the cell membrane, and starts the depolarization process when the membrane potential reaches the threshold. This causes the original action potential machinery (Nav, Kv, and HCN) to excite the cell.

As shown by previous experiments, high expression of ChR2 helps the activation of SGNs, but also changes the intrinsic electrophysiological properties, like the voltage threshold of that cell. Experiments also show that both ChR2 and Chronos, and even other opsins available currently are not fast enough to fit the requirement to deliver auditory information.

The new methods and systems described herein are based on an alternative way to use optogenetic stimulation in a cochlear implant, which is a dual-mode stimulation. This new stimulation mode is based on the combination of electrical cochlear stimulation and new optical (optogenetic) stimulation as a helper stimulus to lower the electrical threshold. This new co-stimulation paradigm will reduce the electrical current magnitude required to excite the cochlear nerves, and removes the crosstalk between adjacent electrodes.

The whole cell recording results described below have provided evidence that supports this hypothesis, because the experiments demonstrate the successful excitation of a spiral ganglion neuron by lowering its electrical voltage threshold by optogenetic depolarization.

Bimodal Hybrid Cochlear Implants and Electrodes

A cochlear implant is an electronic device that is used to improve hearing in humans who have experienced hearing loss, particularly severe to profound hearing loss. These devices typically include an "external" and an "internal" part. The external part (also known as a "speech processor") includes a microphone, and can be placed behind or within the ear (or under the skin) to detect sounds in the environment. The speech processor also includes a small computer that digitizes sounds and processes these digitized sounds. The external components may be referred to as a "processor unit." In addition to the microphone and speech processor, the external portion of the implant can include a power source, such as a battery, and an external antenna transmitter coil. A headpiece that is wired to the speech processor houses a magnet that is of opposite polarity to the surgically implanted device called the receiver-stimulator.

The internal part is an electronic device that is put under the skin in the vicinity of the ear and is commonly referred to as a "stimulator/receiver unit" (see FIGS. 1, 2A, and 2B). The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil, which is positioned to communicate with the implanted antenna receiver coil provided with the stimulator/receiver unit. The communication is typically provided by a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an implant electrode assembly, which applies the electrical and optical stimulation (e.g., with blue light, e.g., about 473 nm) directly to the auditory nerve producing a hearing sensation corresponding to the original detected sound. The optical stimulation should be applied prior to the electrical stimulation.

As shown in FIGS. 2A and 2B, the bimodal hybrid implants as recited herein include an elongated flexible housing sized to fit within a human or animal cochlea; a wire extending through said housing to carry an electrical signal; a plurality of electrodes (electrode bundle) arranged within the housing and so that at least the ends of the electrodes (metallic ends) are situation on an external surface of the flexible housing, e.g., arranged in a linear array, and in electrical contact with the wire inside the housing; a plurality of light emitting diodes (LEDs), e.g., in a ring around the electrode wire (as shown in the top planar view of FIG. 2B), in electrical contact with the wire and arranged on the flexible housing to emit light onto tissue within the cochlea when implanted into the cochlea; and a controller or stimulator linked to the wire and arranged to control emission of electrical signals from the electrodes and light signals from the LEDs. Both the array of electrodes in the electrode assembly as well as an array of light emitting diodes (LEDs) are controlled by the stimulator so that the implant emits both electrical signals and light signals, e.g., blue light, e.g., at a wavelength of about 473 nm, with the optical signals preceding or preceding and overlapping with the electrical signal.

The new multimodal hybrid cochlear implants are inserted into the inner ear in a manner similar to typical cochlear implants. The implant electrode can be made up of a bundle of wires/electrodes, one for each of the external electrodes in the array spread along the length of the implant, and each electrode represents a different frequency of sound. The number of electrodes in the array on the surface of the implant can vary from 1 to about 30 electrodes, such as about 5, 10, 15, 18, 20, 22, 24, 26, or 28 electrodes, or more. A similar number of LEDS can be present as well, e.g., one LED per external electrode in the bundle. Alternatively, the light can be carried and emitted from optical fibers that run within the elongated housing and exit the housing (or shine through the housing if transparent or translucent) at regular intervals along the entire length of the housing.

The external components of the cochlear implant can be carried on the body of the implantee, such as in a pocket of the implantee's clothing, a belt pouch or in a harness, while the microphone can be attached to a clip and mounted behind the ear or attached to a piece of clothing, such as a lapel, hat, hairpin, or eyeglasses. Alternatively, the external components can be housed in a smaller unit capable of being worn behind the ear, in the ear, or under the skin. Such a unit can house the microphone, power unit, and the speech processor. In yet another alternative, the components that are traditionally housed externally may be reduced in size to be implanted or worn in the ear (or a combination of both), resembling a hearing aid. For example, the battery and microphone may be housed in a unit worn in the ear, while the speech processor may be implanted behind the ear.

Functionally, cochlear implants attempt to mimic the hair cells of the cochlea. Hair cells are the sensory cells that convert sound-derived mechanical stimulation into electrical signals that are relayed to the brain via auditory ganglion nerve cells (also called auditory neurons). Like hair cells, the cochlear implants described herein stimulate auditory neurons using both electrical and light signals, e.g., electrical pulses and optical or light pulses. The speech processor converts sound of different frequencies to electrical pulses that are delivered wirelessly to the surgically implanted stimulator/receiver unit. The electrical pulses are converted to radiant energy of a specific wavelength (based on the type of opsin that is expressed in SGNs) using LEDs.

The multimodal hybrid multichannel longitudinal array comprised of half-banded metallic contacts (that are coated to increase charge density and reduce impedances) alternating with LEDs is surgically introduced, e.g., via the round window, into the scala tympani of the cochlea with the metallic contacts and LEDs facing the modiolus. The electrical and optical stimulation has to travel through extracellular fluid, connective tissue, scar tissue, bone, and myelinated tissue to reach the auditory neurons, and the resistance created by these obstacles may decrease the effect of the electrical and light stimulation (e.g., by increasing impedances), which can be corrected by increasing the respective stimulation as required for a specific subject. The cochlear nerve can be stimulated using the new implants with electrical only, optical only, and co-stimulation using both electrical and optical pulses to improve spectral resolution and to provide loudness sensation.

The multimodal hybrid cochlear implant described herein can be implanted in any way traditional, unmodified implants are implanted (e.g., into the scala tympani). Alternatively, the modified implant can be positioned outside the cochlea, but in close vicinity to the auditory nerve. For example, if the auditory nerve is degenerated (e.g., due to trauma or genetic disorder), the implant can be positioned near the pathway of the lost auditory nerve fibers.

Treatment Methods

Treatment methods include implanting a modified cochlear implant into a subject who has a hearing loss to improve the ability of the subject to hear. Any human or animal subject experiencing hearing loss is a candidate recipient of a modified cochlear implant. A human having hearing loss can hear less well than the average human being, or less well than on a prior occasion (e.g., less well than in years past or than before an injury). For example, hearing can be diminished by at least 5, 10, 30, 50% or more. The human can have mild hearing loss (e.g., difficulty hearing sounds below an intensity range of about 20 dB to 40 dB), moderate hearing loss (e.g., difficulty hearing sounds below an intensity range of about 40 dB to 60 dB), severe hearing loss (e.g., difficulty hearing sounds below an intensity range of about 60 dB to 80 dB) or profound hearing loss (e.g., difficulty hearing sounds below an intensity range of about 80 dB or higher).

The human or animal can have sensorineural hearing loss, which results from damage or malfunction of the sensory part (the cochlea) or the neural part (the auditory nerve) of the ear, or conductive hearing loss, which is caused by blockage or damage in the outer and/or middle ear. Alternatively, the human can have mixed hearing loss, which is caused by a deficit in both the conductive pathway (in the outer or middle ear) and in the nerve pathway (the inner ear). An example of a mixed hearing loss is a conductive loss due to a middle-ear infection combined with a sensorineural loss due to damage associated with aging. The human or animal can have unilateral or bilateral hearing loss (loss of hearing in one or both ears, respectively). To merit the use of an implanted device, the loss of hearing in the human is likely to be so severe that an external hearing aid does not improve hearing.

The devices, compositions, and methods described herein are appropriate for the treatment of hearing disorders resulting from sensorineural hair cell loss or auditory neuropathy. Humans or animals subjects with sensorineural hair cell loss experience the degeneration of cochlear hair cells, which frequently results in the loss of spiral ganglion neurons in regions of hair cell loss. Such subjects may also experience loss of supporting cells in the organ of Corti, and degeneration of the limbus, spiral ligament, and stria vascularis in the temporal bone material. Subjects with auditory neuropathy experience a loss of cochlear sensory neurons while the hair cells of the inner ear remain intact.

The subject can be deaf or have a hearing loss for any reason or as a result of any type of event. For example, a human can be deaf because of a genetic or congenital defect; for example, a human identified as a candidate for treatment can have been deaf since birth, or can be deaf or hard-of-hearing as a result of a gradual loss of hearing due to a genetic or congenital defect. In another example, a human identified as a candidate for treatment can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss. A human can experience chemical-induced ototoxicity, wherein ototoxins include therapeutic drugs including antineoplastic or chemotherapeutic agents, salicylates, quinines, and aminoglycoside antibiotics, contaminants in foods or medicinals, and environmental or industrial pollutants. A human can have a hearing disorder that results from aging or that is associated with a disease or disorder such as Meniere's disease, multiple sclerosis, a brain tumor or a stroke.

Human candidate recipients of the modified cochlear implants described herein can be any age including children (e.g., children about 12 months through 18 years) and adults over 18 years of age. The modified cochlear implants may be especially beneficial to hearing-impaired children between the ages of two and three, as it is around this age that language skills develop the fastest.

The multimodal, e.g., bimodal cochlear implants described herein can be implanted in a human by any method known in the art. For example, implantation can be performed under general anesthesia. Generally, an incision is made behind the ear to expose the mastoid bone, which is then removed to allow identification of the facial nerve and the cochlea. An opening is then created in the cochlea to allow insertion of the electrode and LED arrays on the surface of the implant. An insertion tool, or stylet, can be used to facilitate placement of the electrode array inside the cochlea. To secure the implanted processor and to reduce the prominence of the processor on the side of the head, a bony depression can be drilled in the designated position of the internal processor (typically above and behind the outer ear).

A permanent suture, Gortex sheeting, or any of a variety of other means known in the field of cochlear implantation can be used to secure the device into position. The skin incision can then be closed using sutures, such as absorbable sutures, and a compression/protective head wrap can be applied for 1, 2, or 3 days or more to allow time for the skin incision to heal. The initial activation of the implant may be delayed from 2, 3, 4, 5, or 6 weeks or more after surgery, to allow more time for recovery. The electrodes may be activated in small batches, such that activation of all the electrodes will occur over a period of several days or weeks.

A period of rehabilitation may follow activation of the electrodes to build hearing, speech and language skills. Rehabilitation sessions may occur weekly, bimonthly, monthly or periodically over the course of up to a year or more. The rehabilitation regimen can be maintained for 5 months, 6 months, 8 months, one year, or longer.

Before and after implantation of the multimodal cochlear implant, and throughout a course of rehabilitation, the subject can be tested for an improvement in hearing. Methods for measuring hearing are well known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Brainstem evoked response audiometry (BERA or ABR) can also be performed. In BERA, sounds are placed in the ear, and the brainstem's response is recorded from electrodes taped to the patient's head. Electrocochleography can be used to provide information about the functioning of the cochlea and the first part of the nerve pathway to the brain.

The efficacy of the treatment methods described herein can be assayed by determining an improvement in the subject's ability to hear. Alternatively, efficacy can be assayed by measuring distortion product otoacoustic emissions (DPOAEs) or compound action potential (CAP). A subject is successfully treated upon experiencing any objective or subjective improvement in their hearing.

Certain imaging techniques can be used to supplement the hearing tests. These include angiography, and magnetic resonance angiography (MRA) in particular, to produce images of the blood vessels to the brain, and SPECT or PET scans, which produce images of microscopic blood flow within the brain.

EXAMPLE

The invention is further described in the following example, which does not limit the scope of the invention described in the claims.

Transgenic Mouse Model Testing

This study established a transgenic mouse model (Bhlhb5-ChR2R-eYFP) to investigate optogenetic control of spiral ganglion neurons (SGNs), and the results showed that optogenetic stimulation can depolarize SGNs and reduce electrical thresholds significantly. The new concept of combined optogenetic and electrical stimulation for a multichannel, e.g., multimodal, hybrid cochlear implant is based on the findings described below.

Figure 3B:
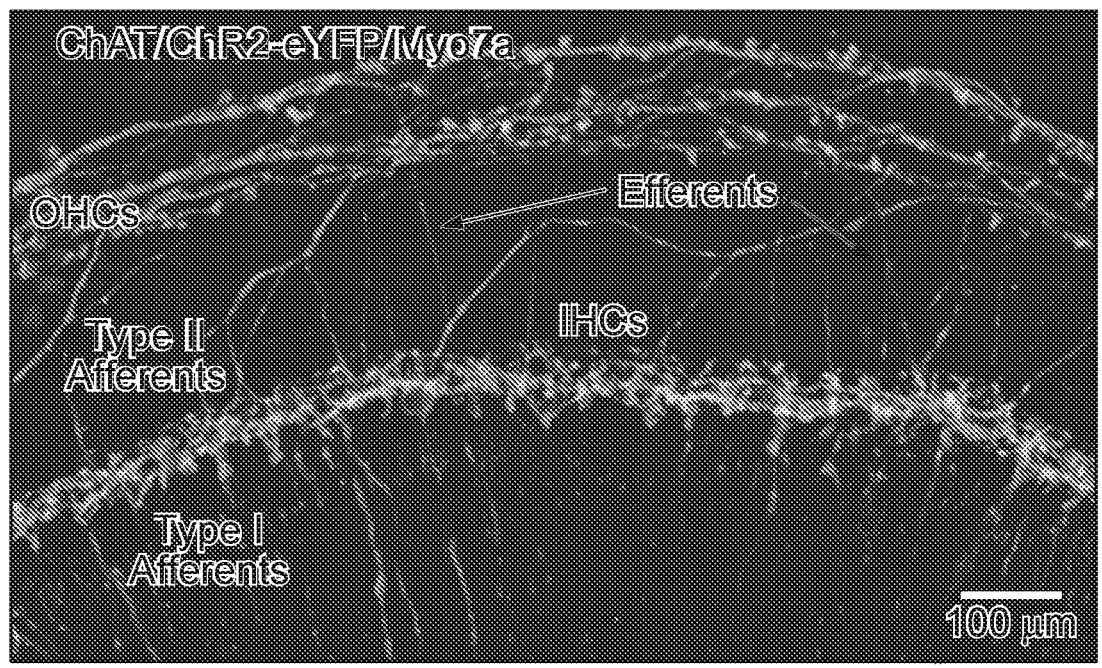

First, a transgenic mouse line was generated as an animal model to examine the responses of auditory nerve or SGNs to acoustic, electrical, or optogenetic stimulation. This mouse line was developed by crossing a Bhlhb5-Cre line (3, 4) with a Cre-dependent, floxed ChR2 line (Ai32) (5). The Bhlhb5-Cre line has a stable and cell type-specific expression in the inner ear (3). This line was crossed with the Ai32 line, which contains a floxed "STOP" cassette upstream of ChR2R in frame with an eYFP gene. These sequences are targeted to the Rosa26 locus and driven by a strong and ubiquitous CAG promoter (5). The Cre recombinase deleted the floxed "STOP" DNA sequence upstream of ChR2R-eYFP specifically and permanently in SGNs and the CAG promoter resulted in robust expression of ChR2R-eYFP in SGNs of the cochlea. As shown in FIGS. 3A and 3B, one can clearly see ChR2R-eYFP expressed in cell bodies and processes of SGNs. FIG. 3A shows Type I SGNs. FIG. 3B shows Type I and II afferents.

Figure 4A:
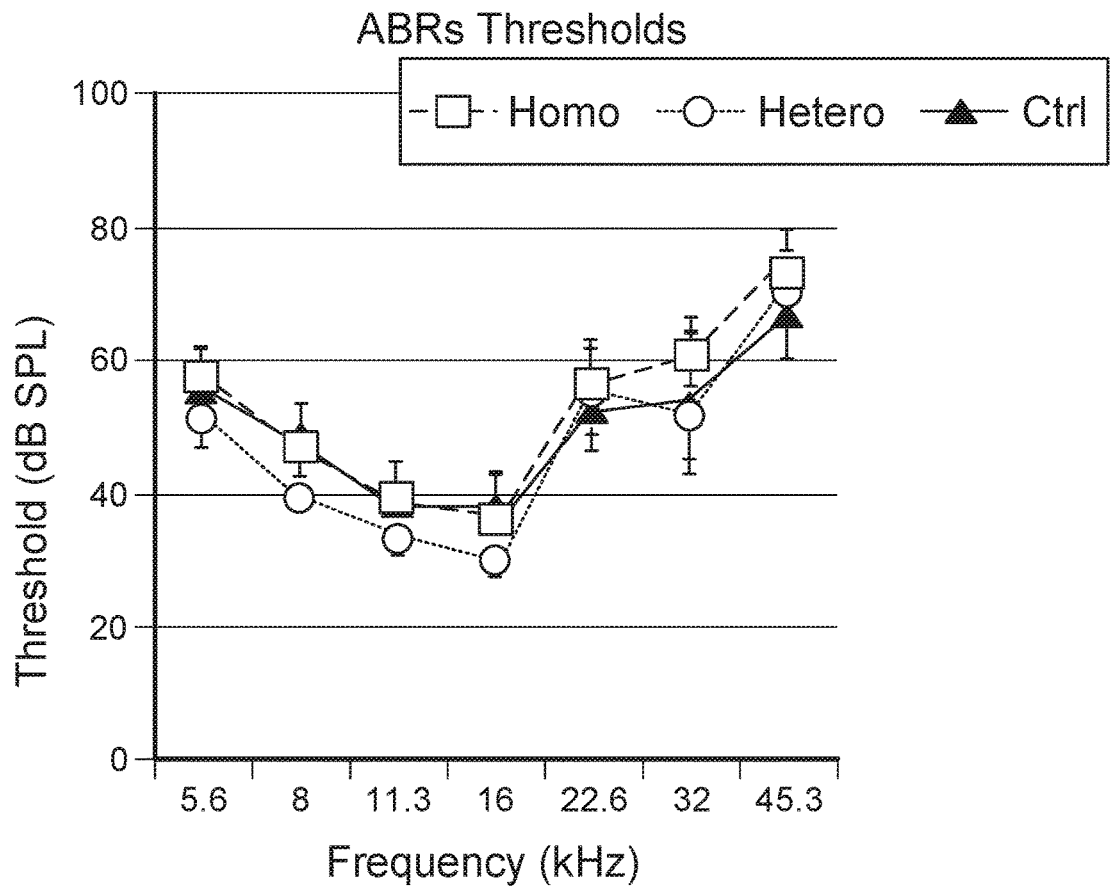
FIGS. 4A-4D are a series of graphs and images of the results of tests done in a transgenic mouse model.
Figure 4B:
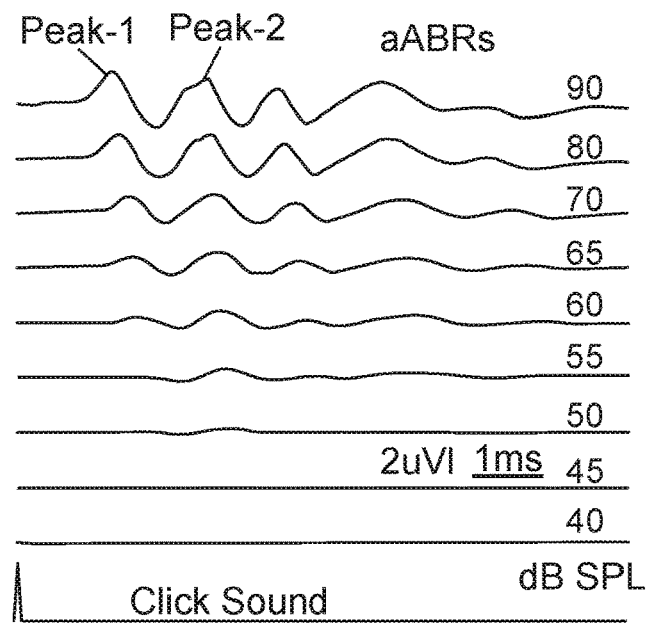
Figure 4C:
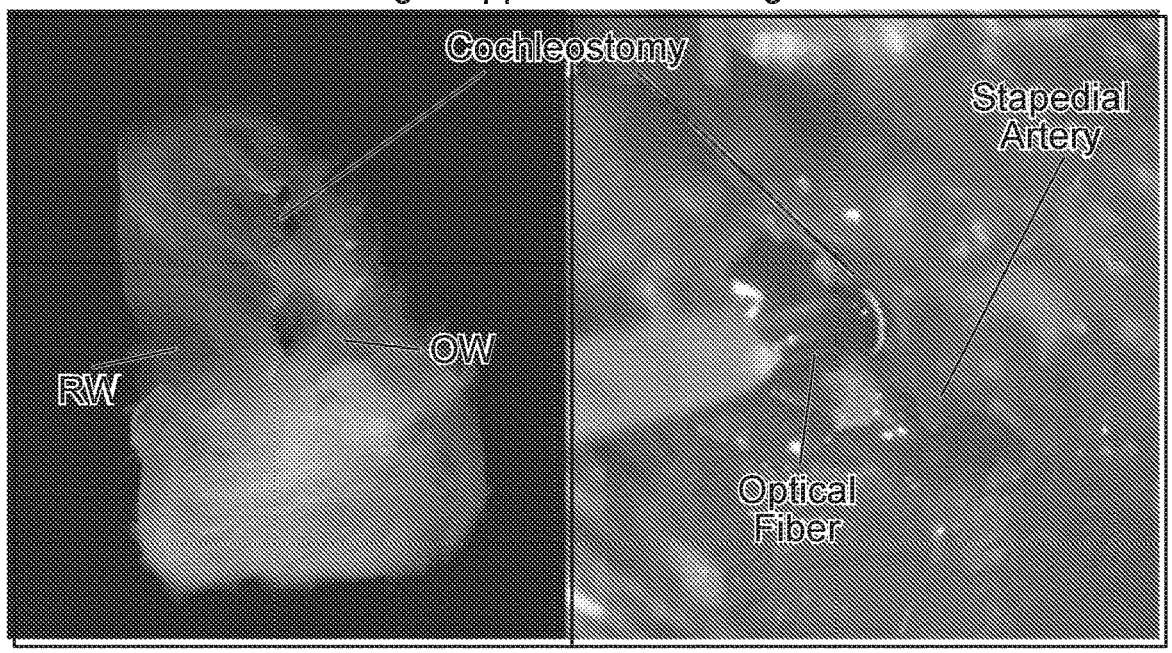
Figure 4D:
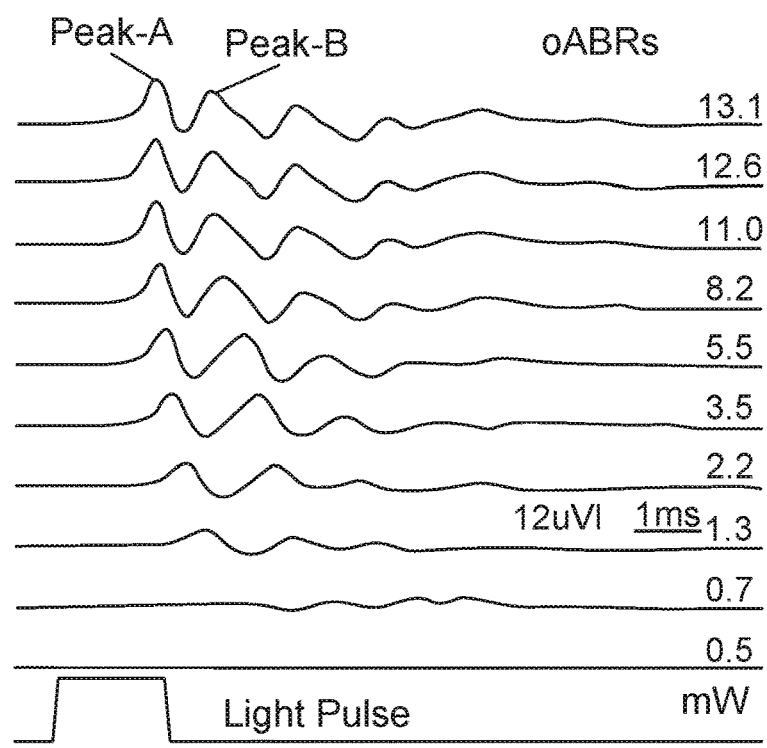

Once the solid expression of ChR2 in SGNs of the cochlea was confirmed, the next step was to examine the responses of auditory nerves to optical stimulation (473 nm blue light pulses). Optically-evoked auditory brainstem response (oABR) was observed in adult mice in response to pulsed blue light provided by an optical fiber guided through a cochleostomy (FIG. 4C). In addition, FIG. 4B shows ABRs after a click stimulus. FIG. 4D is an image of the light application paradigm in the mouse model. In particular, FIG. 4D shows a series of ABRs after a light pulse has been applied. Robust oABRs were elicited in all ChR2R-eYFP positive ears including homozygous and heterozygous (in terms of copies of ChR2R-eYFP genes in genome) mice. At the same time, the acoustic thresholds appeared normal and were not significantly influenced by ChR2R-eYFP expression in these ears (FIG. 4A). FIG. 4A is a graph showing ABR thresholds versus pure tone frequencies. A typical oABR waveform comprised five peaks in the first 8 ms (FIG. 4D), and is comparable to the acoustically-evoked ABR (aABR) (FIG. 4C).

Figure 5A:
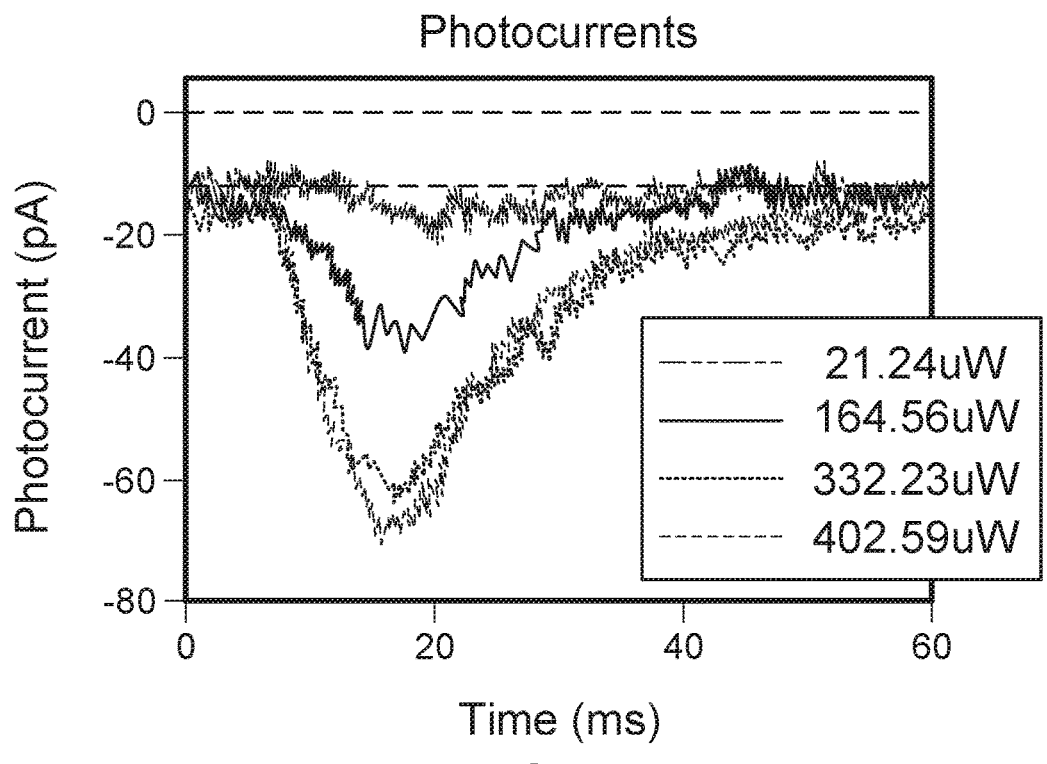
FIGS. 5A-5D are a series of graphs and a photo that shows the optogenetic excitation and sub-threshold control in the mouse model. The optogenetic threshold is defined as the light level to generate an action potential $\theta o=164.56$ uW.
Figure 5B:
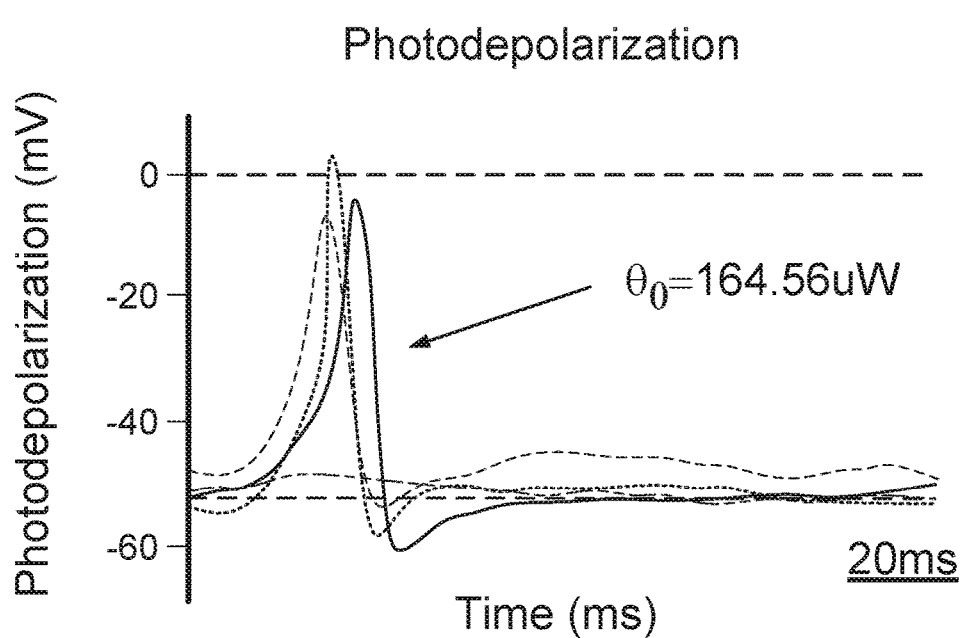
Figure 5C:
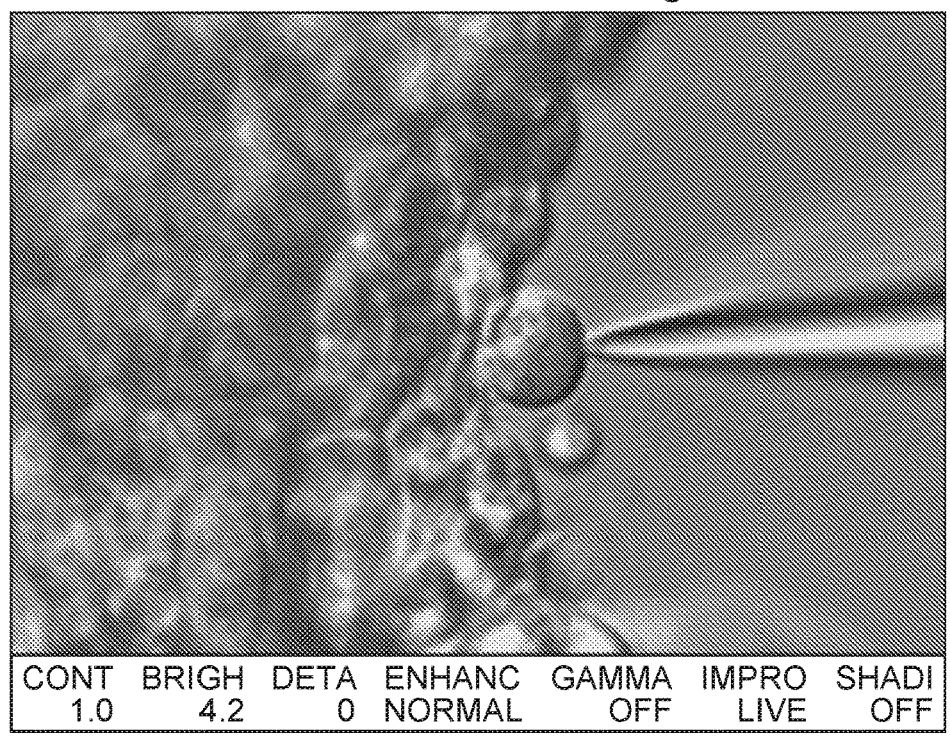
Figure 5D:
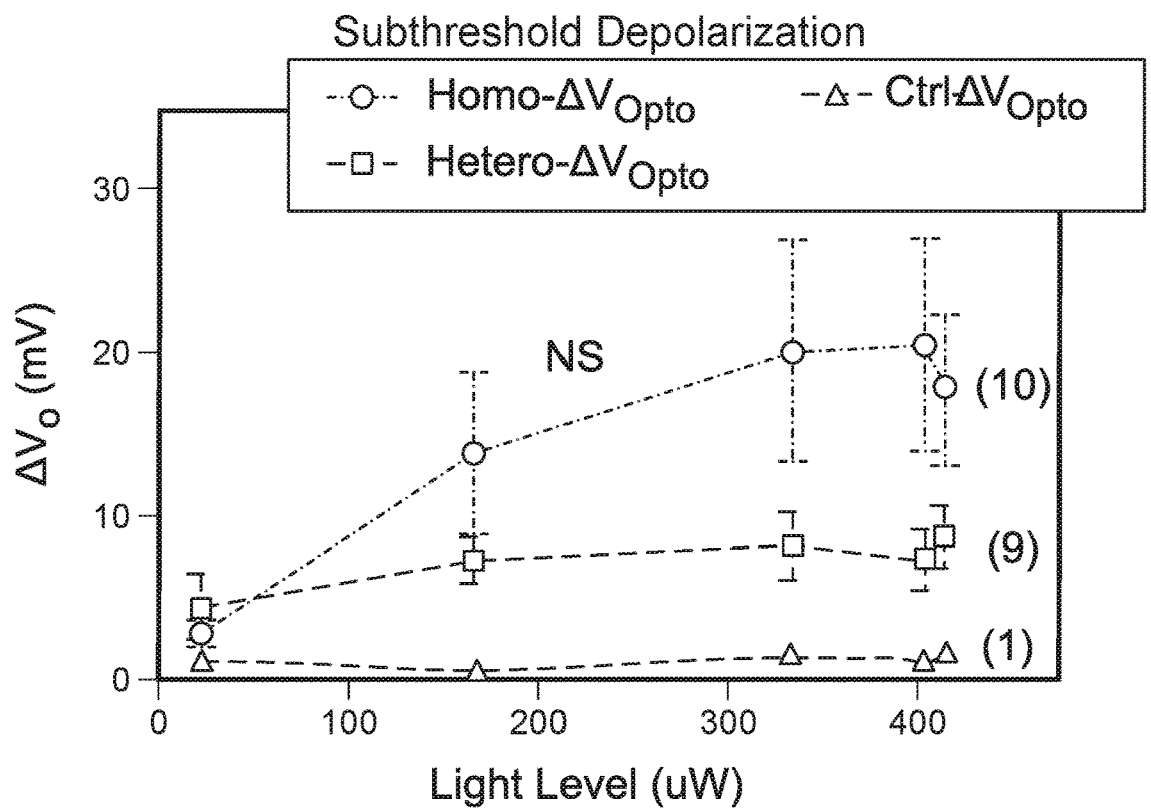

To characterize the photoactivation process at the cellular level, SGN responses to light were tested using whole-cell recording (FIG. 5C). FIG. 5C is a microscope photo of whole cell recording on the SGNs. Significant photocurrents (FIG. 5A) and photodepolarization (FIG. 5B) were observed in most of the SGNs expressing ChR2R-eYFP. The optogenetic activation threshold was defined in this experiment as the minimal light level to successfully evoke an action potential from a SGN cell expressing ChR2R-eYFP. For example, in FIG. 5B, the optogenetic threshold was defined as the light level to generate an action potential $\theta o = 164.56$ μW. From FIG. 5B, the photodepolarization can be divided into two states: supra-threshold photodepolarization and sub-threshold photodepolarization. From, FIG. 5D, which is a graph of sub-threshold depolarization, one can see that the magnitude of sub-threshold photodepolarization increased when the light level increased.

Figure 6A:
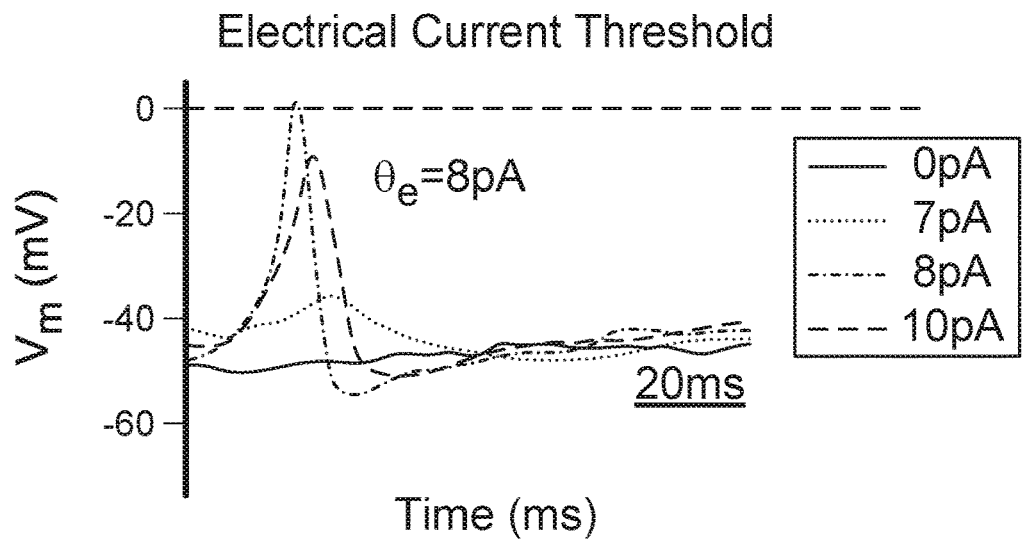
FIGS. 6A-6B are graphs that show electrical excitation and thresholds. The electrical threshold is defined as the current level to generate an action potential, $\theta e=8$ pA.

These findings supported the next test, which used optogenetic stimulation to modulate the electrical threshold of auditory nerves in adult mice, and eventually generated the idea of co-stimulation and the design of a bimodal hybrid cochlear implant for use in human subjects. The electrical threshold ($\theta_e$) was defined as the current level to generate an action potential, for example, in FIG. 6A, this was set to $\theta_e = 8$ pA. Each SGN cell has its specific electrical threshold (2), and the membrane potential has to overcome that threshold to achieve its activation (FIG. 6A). FIG. 6A is a graph of electrical current threshold.

Figure 6B:
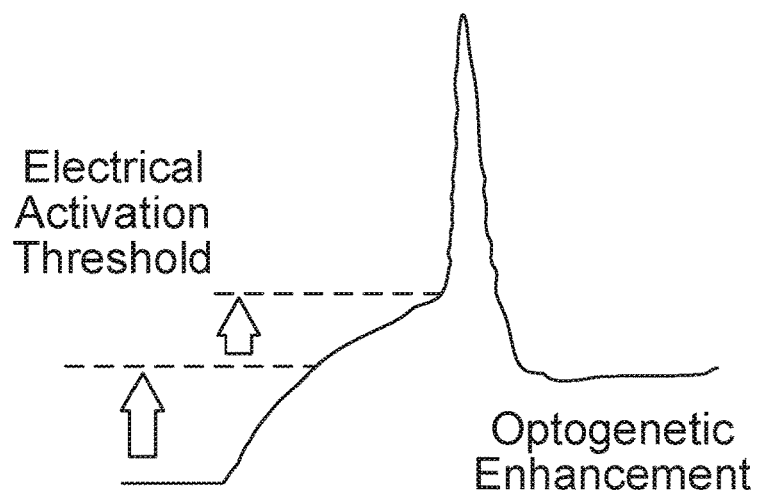

In human subjects, due to this threshold in auditory nerves, the electrical current applied by a single cochlear implant channel spreads vastly to the cochlear spiral and generates cross-talk between adjacent electrodes. To reduce the current level applied and limit the effective spread area in the modiolus, we proposed to use sub-threshold optical stimulation to potentiate the membrane potential to a certain level first, and then add the electrical pulses in a specific time manner, so these electrical pulses can depolarize the membrane further, as shown in FIG. 6B, and then eventually excite SGNs at smaller intensity levels. FIG. 6B is a graph of sub-threshold optogenetic facilitation. This paradigm of stimulation is called opto-electrical co-stimulation.

Figure 7A:
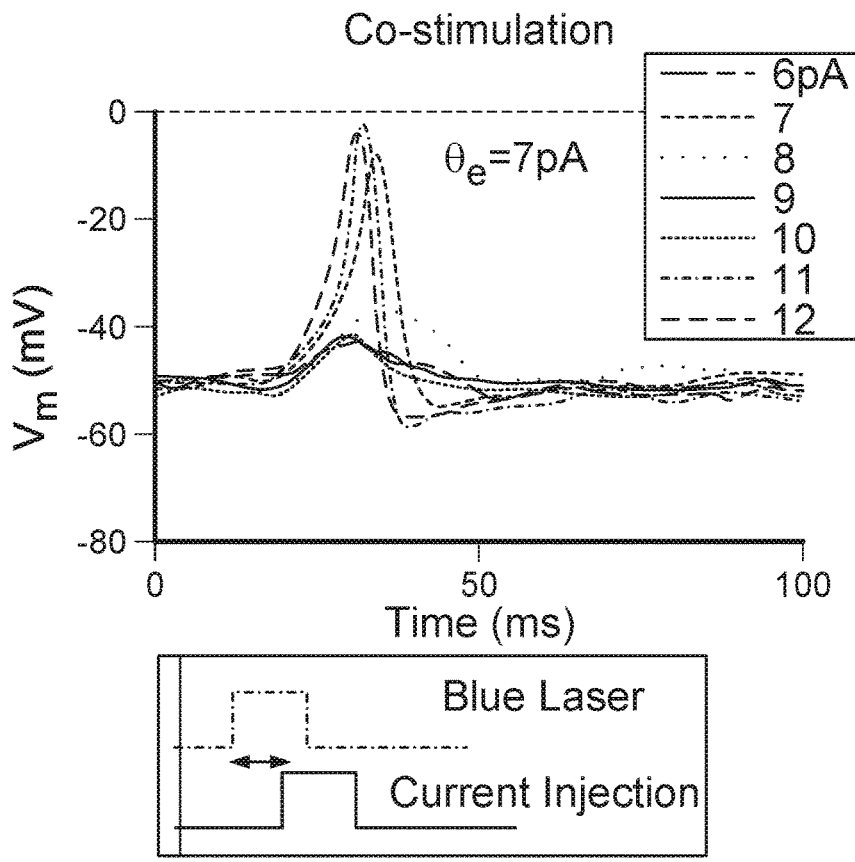
FIGS. 7A and 7B show the results of co-stimulation experiments.

The co-stimulation paradigm can enhance the sensitivity of SGNs to electrical currents, and can effectively reduce the electrical threshold with the help of a sub-threshold optical stimulation. To support this conclusion, we performed whole cell recording experiments in single SGNs, and tested the electrical thresholds of SGNs under blue light pulses or in dark. As shown in FIG. 7A, a 10 ms long electrical current pulse was injected into the SGN, and a 10 ms long blue light pulse (about 473 nm) was presented to the cell ahead of the electrical pulse with different time intervals (0, 2 ms, or 5 ms). These light pulses were presented at two levels: 413 μW (2.5V) and 429 μW (5V). FIG. 7A is a graph that shows sub-threshold blue light pulses (21.24 μW) together with current injection.

Figure 7B:
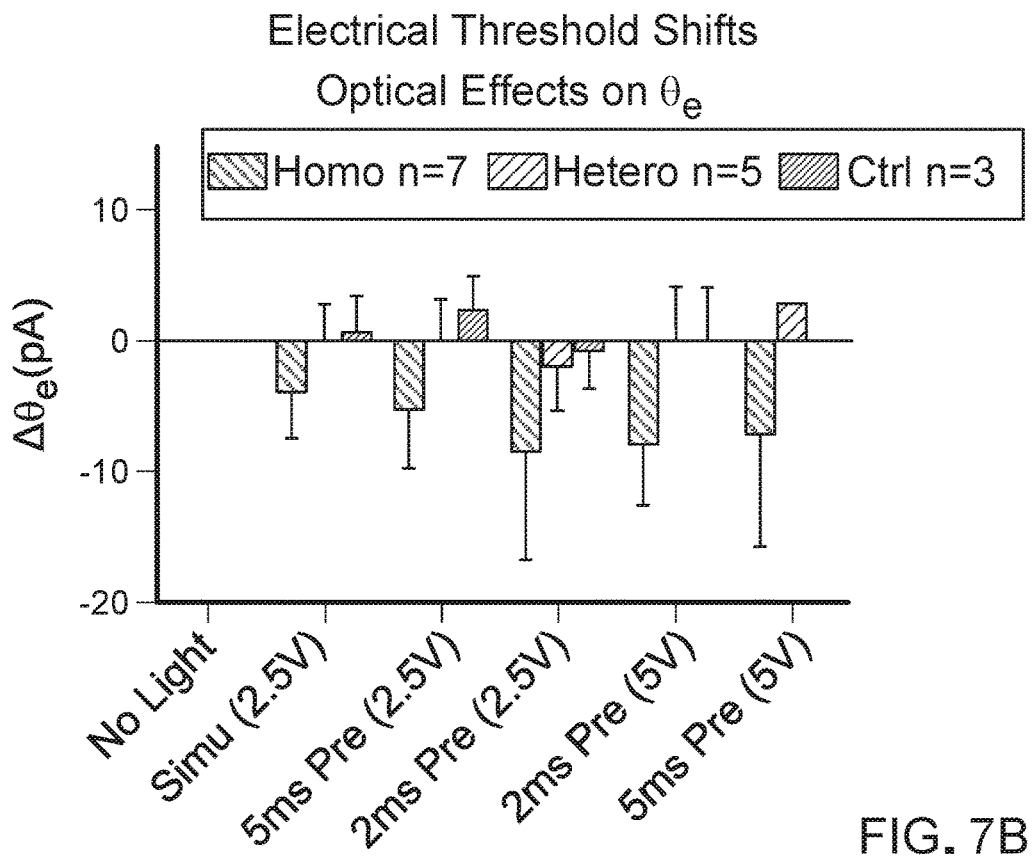

All of these light levels had been tested on the same cell with no electrical current injection, and could not evoke any action potentials. When these sub-threshold light pulses were applied to the cell ahead of the current injection, we found the electrical thresholds were reduced significantly in the homozygous SGN cells, which had more ChR2R-eYFP expression (FIG. 7B). FIG. 7B is a graph that indicates electrical threshold shifts and shows the results of several co-stimulation conditions that were tested: No light; "Simu" means light and current were applied at the same time; or light was presented ahead of current injection 2 or 5 ms earlier at two levels: 413 μW (2.5V) and 429 μW (5V).

Figure 8A:
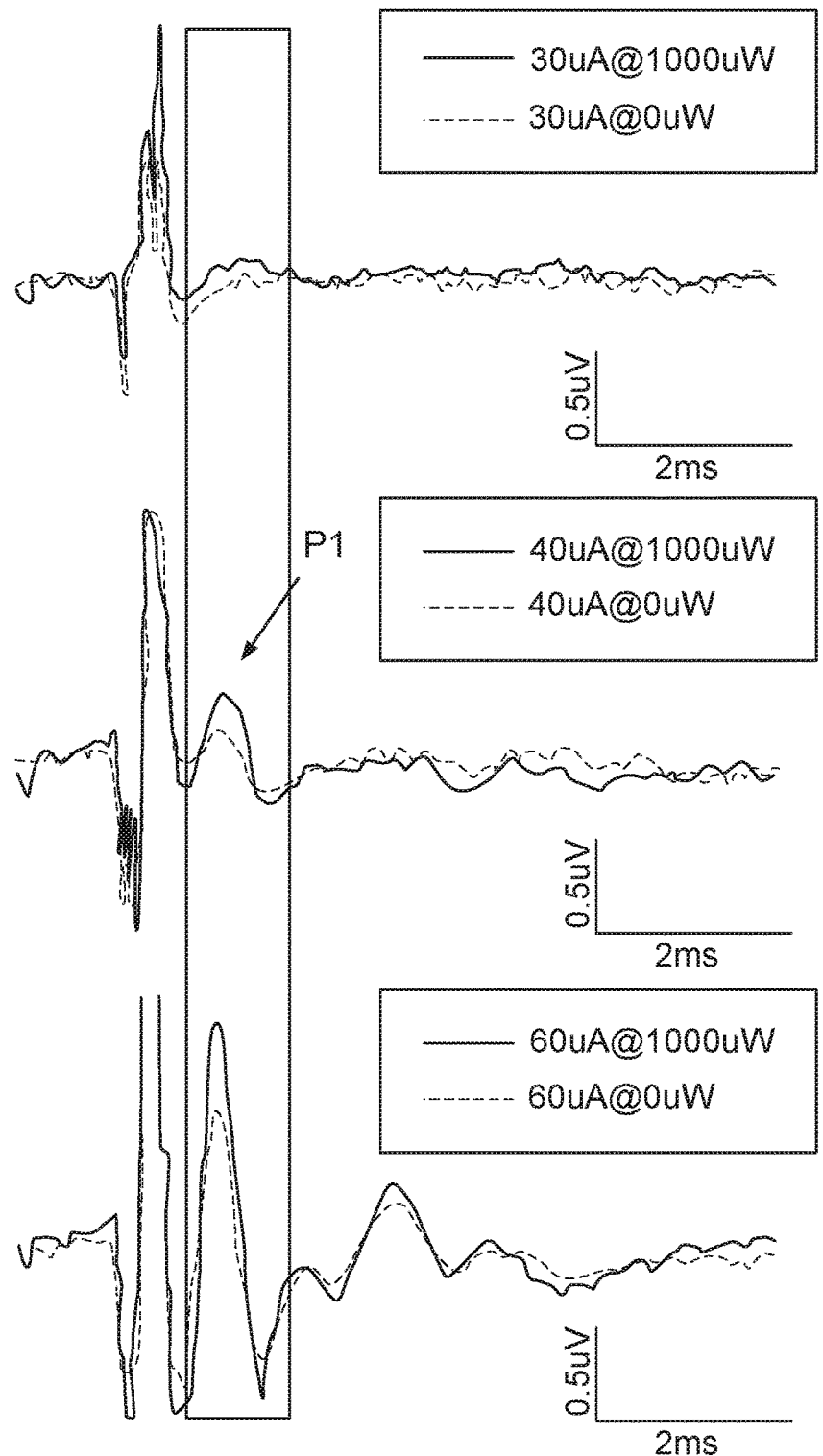
FIGS. 8A-8D are graphs and images of measurement of electrical Auditory Brainstem Response (ABR) thresholds. Sub-threshold blue light pulses (1 mW) were applied.
Figure 8B:
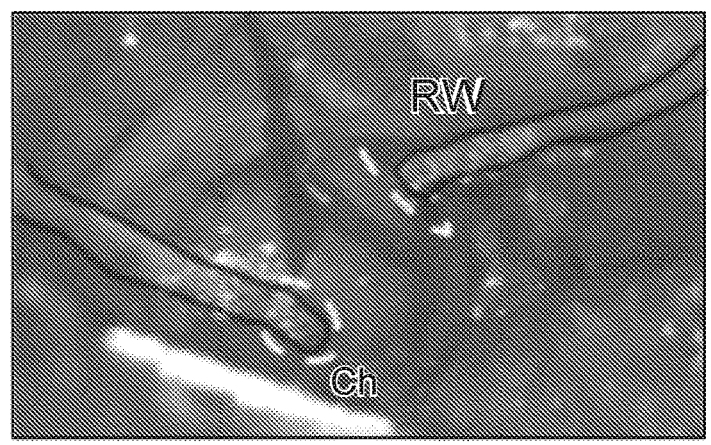

We further tested the co-stimulation paradigm in live adult animals. We used a pair of silver wire electrodes, inserted into the round window and a small hole on the lateral wall of the middle turn, to present the electrical current pulses, and an optical fiber right on top of the lateral wall between the hole and round window to give the blue light stimulation (FIGS. 8A and 8B). FIG. 8A is a series of graphs that show co-stimulation. FIG. 8B is an image showing electrode placement.

Figure 8C:
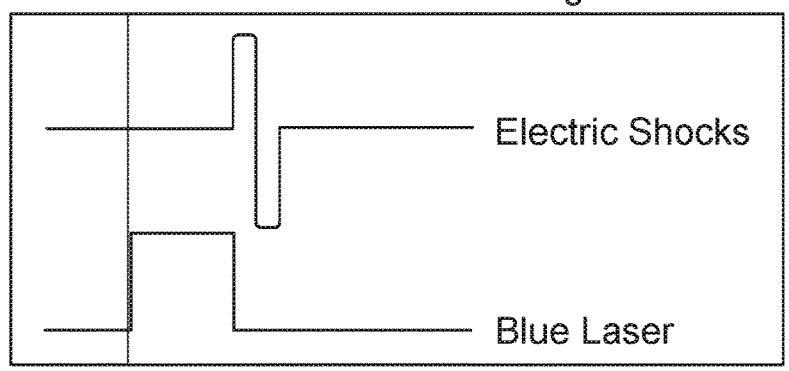
Figure 8D:
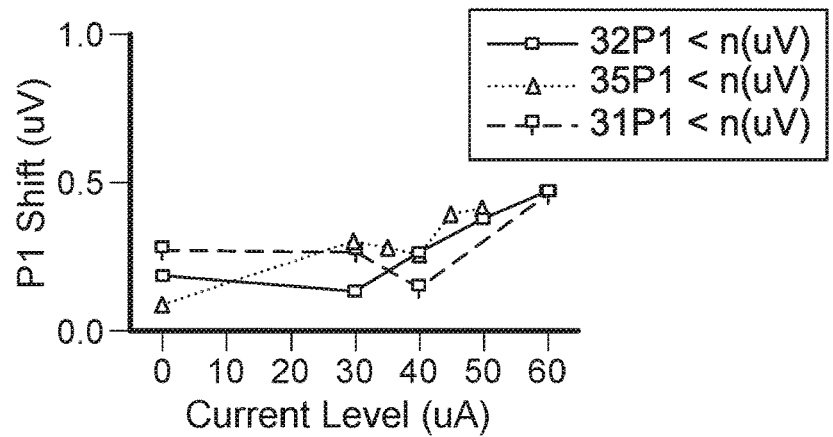

An example of co-stimulation paradigm is illustrated in the graph of FIG. 8C, in which a 1 ms long blue light pulse (1 mW) was applied and followed by application of an electrical shock (100 μs pulse width). We found this electrical shock can easily elicit an electrically-evoked ABR (eABR) response when the current level was greater than 30 μA, shown in a gray box on red response traces in FIG. 8A. When we combined the electrical shock with a pre-leading light pulse at 1 mW level, the magnitude of electrical responses (amplitude of peak 1, P1) were successfully enhanced, compared to the blue traces with no light stimulation. The amplitude-shifts of peak 1 caused by the blue light pulses in three animals are illustrated in FIG. 8D. FIG. 8D is a graph showing P1 amplitude shift vs. current level.

These results demonstrate the potentiation of electrical responses from a weak light level, and support the conclusions developed from the whole cell recording studies.

Figure 9A:
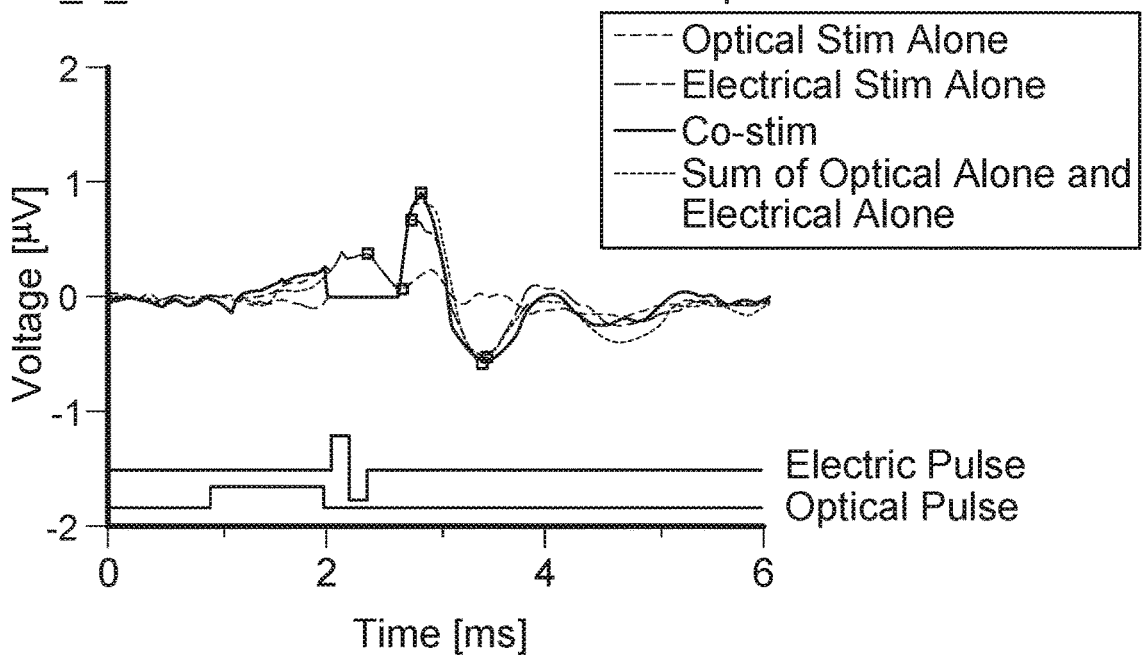
FIGS. 9A-9D are a series of graphs that show that the co-stimulation response approximates the summation of oABR and eABR amplitudes.
Figure 9B:
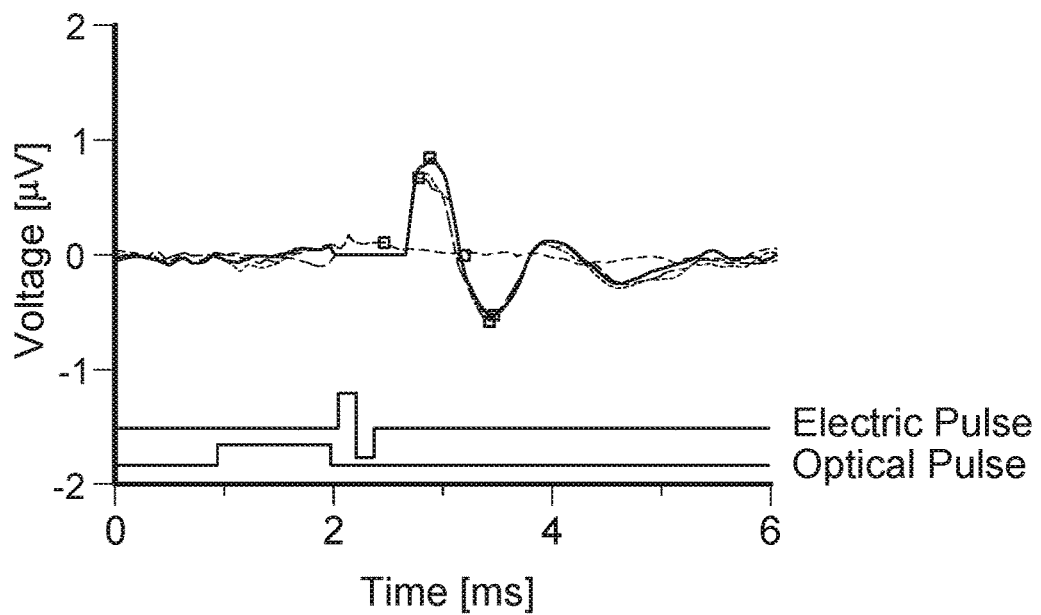
Figure 9C:
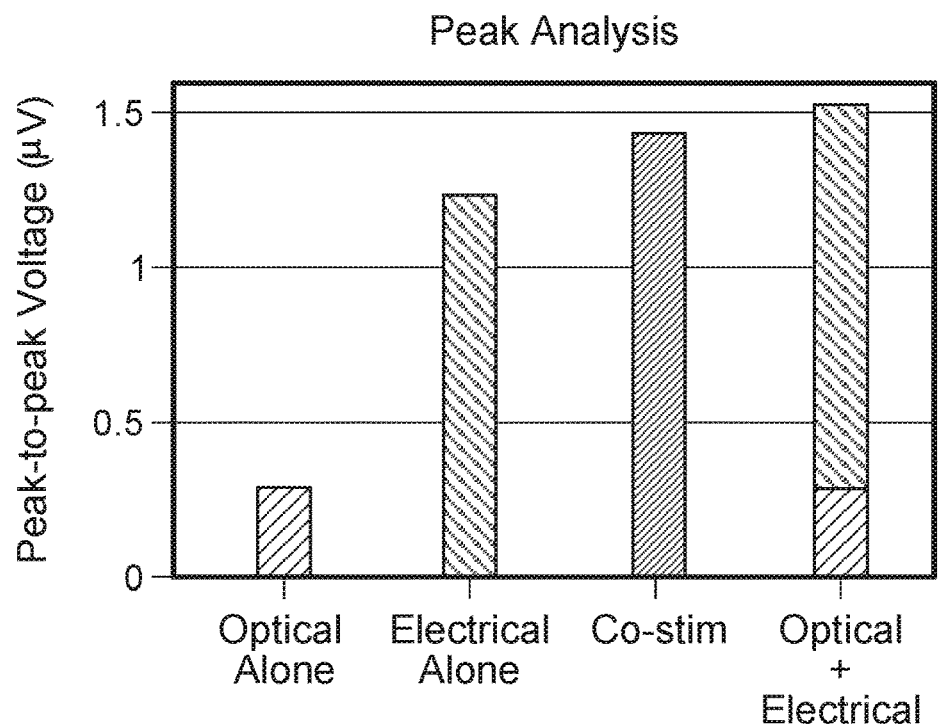
Figure 9D:
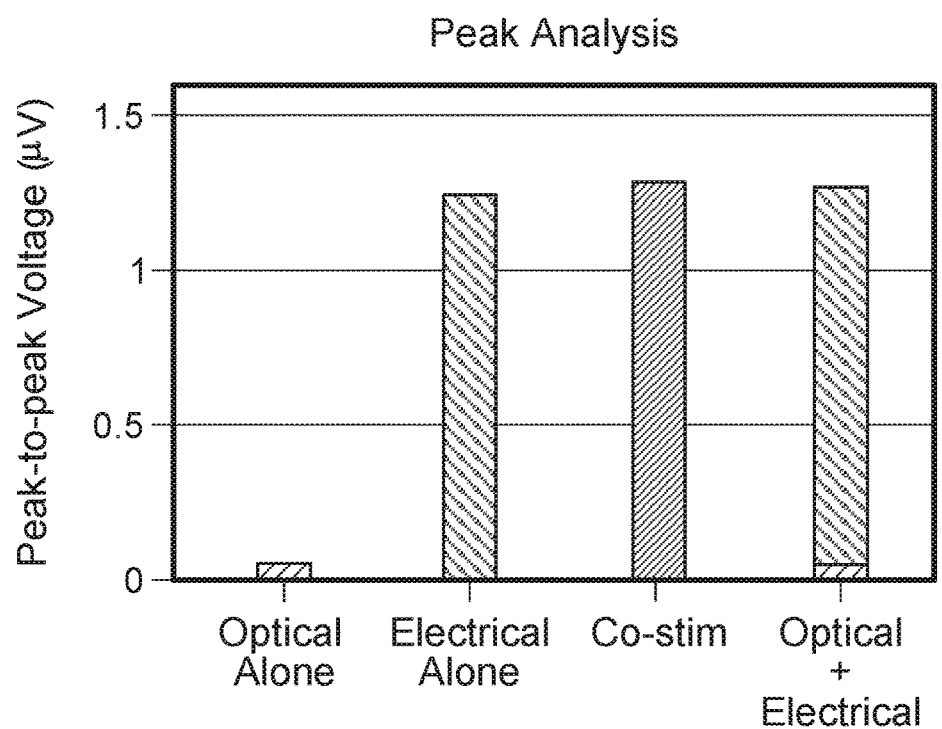

Based on the whole cell recording studies, it is clear that the timing of stimulus presentation is crucial to a successful co-stimulation. Thus, we fixed the electrical current level at 60 μA, and presented the light pulses prior to or right after the electrical shock to the ears in three adult Bhlhb5-ChR2R-eYFP mice. We examined ABR responses to our co-stimulation paradigm at a supra-threshold level. When the 1 ms long blue light pulse at different levels was presented prior to the electrical shock (FIGS. 9A and 9B), the responses to the co-stimulation paradigm can always approximate the summation of oABR and eABR amplitudes (FIGS. 9C and 9D).

Figure 10A:
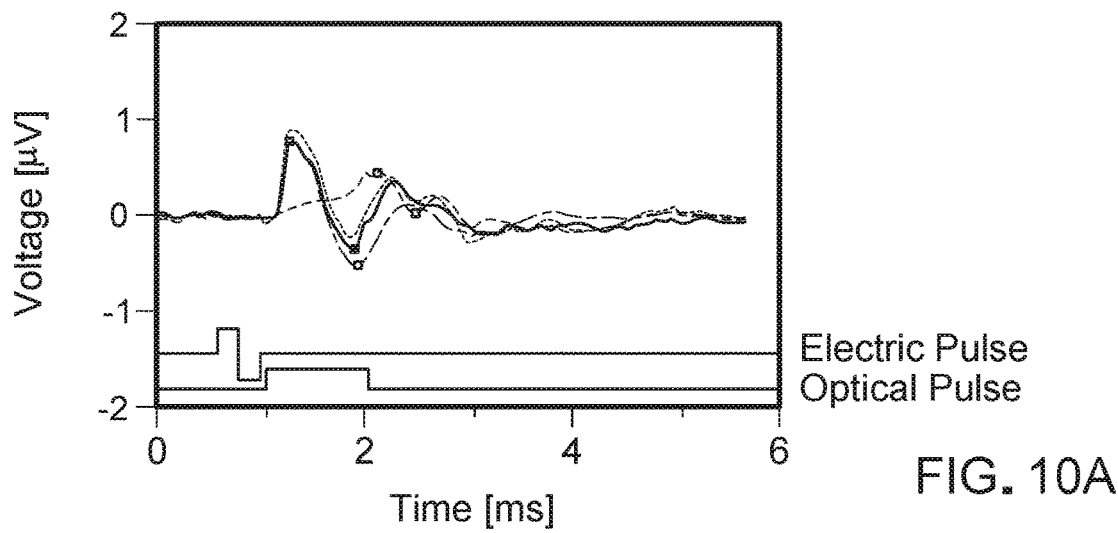
FIGS. 10A-10C are a series of graphs that show that the timing of stimulus presentation is important to proper summation.
Figure 10B:
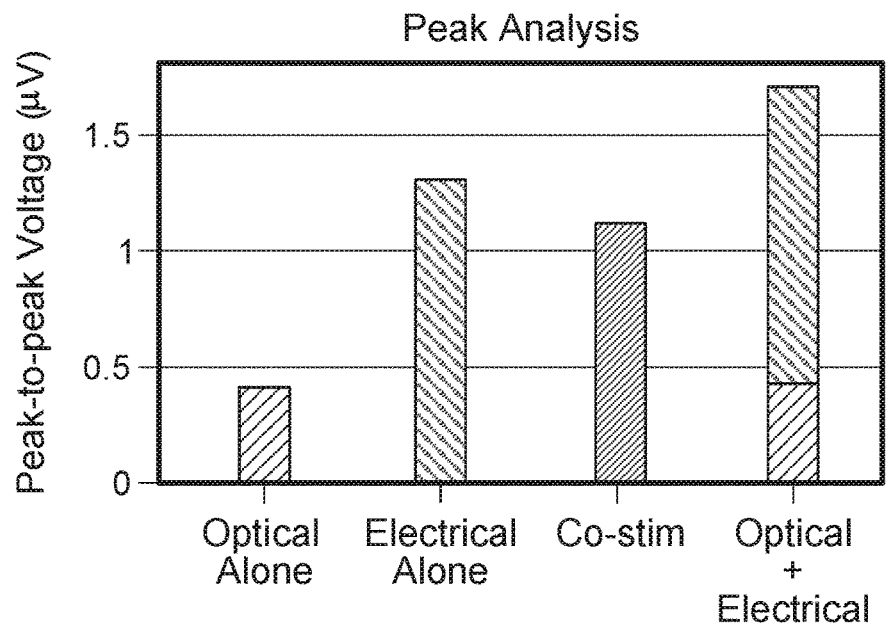
Figure 10C:
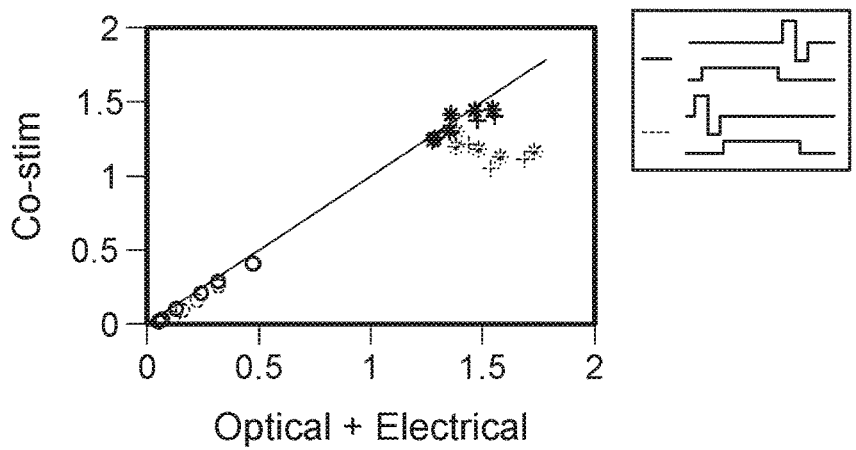

However, when the light pulse was presented following the electrical shock (FIG. 10A), the response to the co-stimulation paradigm was significantly smaller than the summation of oABR and eABR magnitudes when light and electrical pulses were applied alone (FIG. 10B). When we plot the peak amplitudes of ABR responses obtained from co-stimulation paradigm against the sum of the peak amplitudes from either modality alone, we can see that the co-stimulation paradigm with the light pulses ahead of its electrical shocks achieves greater responses compared to those evoked by a co-stimulation with the light pulses followed the shocks (FIG. 10C). All comparisons were done between the responses evoked by optical or electrical stimulus at the same levels. These findings indicate that the helper light pulse should be applied prior to the electrical pulse to achieve the most efficient potentiation of electrical activation of auditory nerves.

REFERENCES

1. V. H. Hernandez et al., "Optogenetic stimulation of the auditory pathway," J. Clin. Invest., 124, 1114-1129 (2014).

2. Q. Liu, E. Lee, R. L. Davis, "Heterogeneous intrinsic excitability of murine spiral ganglion neurons is determined by Kv1 and HCN channels," Neuroscience, 257, 96-110 (2014).
3. J. M. Appler et al., "Gata3 is a critical regulator of cochlear wiring," J. Neurosci., 33, 3679-3691 (2013).
4. N. R. Druckenbrod, L. V. Goodrich, "Sequential Retraction Segregates SGN Processes during Target Selection in the Cochlea," J. Neurosci., 35, 16221-16235 (2015).
5. L. Madisen et al., "A toolbox of Cre-dependent optogenetic transgenic mice for light-induced activation and silencing," Nat. Neurosci., 15, 793-802 (2012).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bimodal hybrid cochlear implant comprising an elongated, flexible housing sized to fit within a human or animal cochlea;
   a wire extending longitudinally through the housing to carry an electrical signal;
   an electrode bundle arranged within the housing, wherein each electrode in the electrode bundle is in electrical contact with the wire and wherein the electrodes are arranged such that an end of each electrode exits the housing or can emit an electrical signal through the housing;
   a plurality of light emitters, wherein a ring of light emitters is arranged around each electrode, and is arranged to emit blue light from the housing when implanted into the cochlea; and
   a controller linked to the wire and the light emitters and arranged to control emission of electrical signals from the electrodes and emission of blue light signals from the light emitters, wherein the blue light signals are controlled to be emitted at an intensity to provide a sub-threshold optical stimulation of auditory nerves prior to the electrical signals, and wherein the electrical signals are controlled to be emitted at an intensity to achieve potentiation of electrical activation of the auditory nerves.

2. The implant of claim 1, wherein the array of electrodes comprises a linear array of electrodes.
3. The implant of claim 1, wherein the ends of the electrodes are arranged on an external surface of the flexible housing.
4. The implant of claim 1, wherein the light signal is controlled to be emitted prior to and overlapping with the electrical signal.
5. The implant of claim 1, comprising at least 2 to about 30 electrodes, and at least 2 to about 30 light emitters.
6. The implant of claim 1, wherein the blue light emitters are light emitting diodes (LEDs), and wherein each LED is in electrical contact with the wire and is arranged to emit light from the housing when implanted into the cochlea.
7. The implant of claim 6, wherein the blue light has a wavelength of about 473 nm.
8. The implant of claim 1, wherein the light emitters comprise a light source and a plurality of optical fibers arranged within the housing such that ends of each optical fiber emit light through a wall of the housing or through windows or openings arranged in the wall of the housing, and wherein the controller is linked to the light source.
9. The implant of claim 1, wherein the housing comprises a lumen extending longitudinally within the housing, and the electrode bundle is arranged within the lumen.
10. The implant of claim 1, wherein the blue light has a wavelength of about 473 nm.
11. A method of treating a subject who has experienced hearing loss, the method comprising
    identifying a subject in need of treatment for hearing loss; and
    implanting the bimodal hybrid cochlear implant of claim 1 in the subject.
12. The method of claim 11, wherein the method further comprises determining a level of hearing loss, and determining that the hearing loss is not significantly improved by use of an external hearing aid.
13. The method of claim 12, wherein the hearing loss is severe or profound.
14. The method of claim 11, further comprising conducting a hearing test appropriate for a human child between the ages of about 12 months and 48 months.
15. The method of claim 11, further comprising conducting a hearing test appropriate for an elderly human patient.
16. The method of claim 11, wherein the method further comprises subjecting the subject to a rehabilitation regimen to facilitate hearing, speech, and language skills.

* * * * *